United States Patent
Wang et al.

(10) Patent No.: US 8,697,702 B2
(45) Date of Patent: *Apr. 15, 2014

(54) METHOD OF OPTIMIZING THE TREATMENT OF PHILADELPHIA-POSITIVE LEUKEMIA WITH IMATINIB MESYLATE

(75) Inventors: Yanfeng Wang, Florham Park, NJ (US); Thea Kalebic, Springfield, NJ (US); Timothy P Hughes, South Australia (AU); Deborah White, South Australia (AU)

(73) Assignees: Novartis AG, Basel (CH); Medvet Science Pty Ltd, Underdale (AU)

( * ) Notice: Subject to any disclaimer, the term of this patent is extended or adjusted under 35 U.S.C. 154(b) by 5 days.

This patent is subject to a terminal disclaimer.

(21) Appl. No.: 13/129,903

(22) PCT Filed: Nov. 30, 2009

(86) PCT No.: PCT/US2009/066045
§ 371 (c)(1),
(2), (4) Date: May 18, 2011

(87) PCT Pub. No.: WO2010/065433
PCT Pub. Date: Jun. 10, 2010

(65) Prior Publication Data
US 2011/0224224 A1    Sep. 15, 2011

Related U.S. Application Data

(60) Provisional application No. 61/118,708, filed on Dec. 1, 2008.

(51) Int. Cl.
*A61K 31/497*    (2006.01)
(52) U.S. Cl.
USPC .................................................. 514/252.18
(58) Field of Classification Search
USPC .................................................. 514/252.18
See application file for complete search history.

(56) References Cited

FOREIGN PATENT DOCUMENTS

WO    WO 2008/036792 A2    3/2008
WO    WO 2009/000023 A1    12/2008

OTHER PUBLICATIONS

White et al. (Blood (2007); 110;4064-4072).*
White et al., "Most CML patients who have suboptimal response to Imatinib have low OCT-1 activity: higher doses of imatinib may overcome the the negative impact of low OCT-1 activity", Blood, vol. 110, No. 12, pp. 4064-4072, Dec. 2007.
White et al., "CML patients with Low OCT-1 Activity Achieve Better Molecular Responses on High Dose Imatinib Than on Standard Dose. Those with High OCT-1 Activity Have Excellent Responses on Either Doses: A TOPS Correlative. Study", Blood, vol. 112, No. 11, pp. 1093-1094, Nov. 2008.

* cited by examiner

*Primary Examiner* — Shirley V Gembeh
(74) *Attorney, Agent, or Firm* — Stephen Johnson; George R. Dohmann

(57) ABSTRACT

The present invention relates to a method of treating Philadelphia-positive leukemia (Ph+ leukemia), in a particular chronic myeloid leukemia (CML), in a human patient population. More specifically, the present invention pertains to a method of treating Ph+ leukemia, such as CML or Phi+ ALL, in a human patient suffering from Ph+ leukemia comprising the steps of
(a) administering a predetermined fixed amount of Imatinib as a free base or in the form of a pharmaceutically acceptable salt thereof to the human patient,
(b) collecting at least one blood sample from the patient, e.g. within the first 12 months of treatment,
(c) determining the plasma trough level (Cmin) of Imatinib,
(d) determining the OCT-1 Activity in the blood sample, and
(e) adjusting the dose of Imatinib applied to the individual patient in a manner that an Imatinib Cmin value is achieved in the patient of at least 800 ng/mL, if in step (c) an Imatinib Cmin value of less than 800 ng/mL is found and in step (d) an OCT-1 Activity is found below 6.0 to 10.0 ng/200,000 cells.

6 Claims, No Drawings

METHOD OF OPTIMIZING THE TREATMENT OF PHILADELPHIA-POSITIVE LEUKEMIA WITH IMATINIB MESYLATE

This application is a 371 of PCT/US2009/066045 filed on Nov. 30, 2009, which claims benefit of U.S. Provisional Application No. 61/118,708 filed on Dec. 1, 2008, which in their entirety are herein incorporated by reference.

The present invention relates to a method of treating Philadelphia-positive leukemia (Ph+ leukemia) in a human patient population. In a particular aspect, the present invention relates to a method of treating chronic myeloid leukemia (CML) in a human patient population.

In May 2001 the mesylate salt of N-{5-[4-(4-methyl-piperazino-methyp-benzoylamido]-2-methylphenyl}-4-(3-pyridyl)-2-pyrimidine-amine (Imatinib mesylate, STI571B, Glivec®) was approved by the FDA for the treatment of CML in patients who had failed to benefit from IFN-alpha therapy. Glivec became very soon the standard of care for the treatment of CML.

In the International Randomized Study of Interferon and STI571 (IRIS) the therapeutic benefit for CML patients treated with Imatinib mesylate was monitored over several years. In WO2008/036792 a method of optimizing the treatment of Ph+ leukemia is described, which is based on the results of the results of the IRIS and a study conducted at the University of Bordeaux. WO2008/036792 teaches that the treatment of Ph+ leukemia using a Bcr-Abl inhibitor, especially Imatinib mesylate, can be optimized by adjusting the dose of the Bcr-Abl inhibitor applied to an individual patient in a manner that a specific minimum plasma trough level (Cmin) is achieved in that individual patient.

The OCT-1 protein is a member of the largest superfamily of transporters, the solute carrier family (Koepsell H, Endou H. Pflugers Arch. 2004; 447:666-676) which transport in an electrogenic fashion a variety of organic cations, including drugs, toxins and other xenobiotics. The transporter is predicted to have 12 transmembrane domains, and binding pockets with partially overlapping interaction domains for different substrates and inhibitors (Koepsell H, Schmitt B M, Gorboulev V. Rev Physiol Biochem Pharmacol. 2003; 150: 36-90). Post transcriptional regulation of OCT-1 by phosphorylation status (Ciarimboli G, Schlatter E. Pflugers Arch. 2005; 449:423-441) and such compounds as PKA, Src-like p56 and CaM have also been demonstrated.

In a further development of the invention described in WO2008/036792 and on the basis of a further evaluation of the data of clinical studies in CML, including the IRIS study, the present invention provides an improved method for treating Ph+ leukemias in human patients being treated with Imatinib or a pharmaceutically acceptable salt thereof. It was now surprisingly found that CML patients having a low OCT-1 Activity experience a substantially higher therapeutic benefit from the methods described in WO2008/036792 than those having a relatively high OCT-1 Activity. Actually, it was found that the chance of CML patients having an Imatinib Cmin value below the threshold of at least 800 ng/mL blood and at the same time a low OCT-1 Activity have no chance to obtain an MMR at 12 months, which is a critical landmark for successful treatment of Ph+ leukemia with a Bcr-Abl inhibitor such as Imatinib mesylate, whereas an Imatinib Cmin value below the threshold mentioned above has no impact on the treatment outcome for those patients having a high OCT-1 Activity.

CML belongs to the group of Ph+ leukemia. The results obtained with the CML patient population described herein can be transferred directly to the whole group of Ph+ leukemias. The reason for that is that the characterizing feature of Ph+ leukemias is the existence of the Philadelphia chromosome causing the Bcr-Abl fusion protein. The latter protein is the target of all Bcr-Abl inhibitors.

The abbreviation "Ph+ ALL" as used herein denotes Philadelphia chromosome positive acute lymphoblastic leukemia.

The term "major molecular response (MMR)" as used herein means a 3 logarithm reduction in BCR-ABL transcripts, quantified from peripheral blood using real-time quantitative reverse-transcriptase polymerase chain reaction, after, e.g. 12 months Imatinib mesylate therapy.

The term "complete cytogenic response (CCR)" as used herein means 0% Philadelphia-chromosome positive metaphases among at least 20 or 25 cells in metaphase in the bone marrow aspirate (Colombat M, Fort M P, Chollet C, et al. Molecular remission in chronic myeloid leukemia patients with sustained complete cytogenetic remission after imatinib mesylate treatment. Haematologica 2006; 91:162-8.).

The term "method of treatment" as used herein relates also to a method of prevention of the diseases mentioned herein, i.e. the prophylactic administration of a pharmaceutical composition comprising Imatinib mesylate to healthy patients to prevent the development of the diseases mentioned herein.

The terms "adjusting the dose" and "the dose of . . . is adjusted" as used herein preferably denote that the dose referred to is increased or decreased.

OCT-1 Activity as referred to herein is measured in pre-therapy blood from CML patients by calculating the difference in intracellular uptake and retention (IUR) of [$^{14}$C]-Imatinib with and without OCT-1 inhibition. For instance, OCT-1 Activity can be calculated as the difference in IUR in the absence (total IUR) and presence of prazosin, to provide a measure of the actual activity of the OCT-1 protein in the transport of imatinib. For example: [Total IUR 32 ng/200,000 cells)]–[prazosin IUR 23 ng/200,000 cells] gives an OCT-1 Activity of 9 ng/200,000 cells. However, the present invention also embraces corresponding methods employing alternative assays or processes for determining the OCT-1 Activity. Methods for the determination of the OCT-Activity are, for instance, described in Blood, 2007 Dec. 1; 110(12):4064-72.

Hence, the present invention relates to a method of treating Ph+ leukemia, such as CML or Ph+ ALL, in a human patient suffering from Ph+ leukemia comprising the steps of (a) administering a predetermined fixed amount of Imatinib as a free base or in the form of a pharmaceutically acceptable salt thereof, e.g. an oral daily dose of 400 mg or 800 mg of the mono-mesylate salt of Imatinib, to the human patient, (b) collecting at least one blood sample from the patient, e.g. within the first 12 months of treatment, especially the first 3 months, preferably within the first 30 days, (c) determining the plasma trough level (Cmin) of Imatinib, (d) determining the OCT-1 Activity in the blood sample, and (e) adjusting the dose of Imatinib applied to the individual patient in a manner that an Imatinib Cmin value is achieved in the patient of at least 800 ng/mL, if in step (c) an Imatinib Cmin value of less than 800 ng/mL is found and in step (d) an OCT-1 Activity is found below 6.0 to 10.0 ng/200,000 cells, especially 8.0 to 8.5 ng/200,000 cells.

Furthermore, the present invention relates to the use of Imatinib as a free base or in the form of a pharmaceutically acceptable salt thereof for the manufacture of a medicament for the treatment of a Ph+ leukemia, wherein (a) administering a predetermined fixed amount of Imatinib as a free base or in the form of a pharmaceutically acceptable salt thereof to the human patient, (b) collecting at least one blood sample from the patient,
(c) determining the plasma trough level (Cmin) of Imatinib,
(d) determining the OCT-1 Activity in the blood sample, the dose of Imatinib applied to the individual patient is adjusted in a manner that an Imatinib Cmin value is achieved in the patient of at least 800 ng/mL, if in step (c) an Imatinib Cmin value of less than 800 ng/mL is found after administration of the predetermined fixed amount of Imatinib and in step (d) an OCT-1 Activity is found below 6.0 to 10.0 ng/200,000 cells.

Preferably, the Imatinib Cmin level is adjusted to a value between 800 and 3500 ng/mL, more preferably a Cmin between 1000 and 3000 ng/mL. At a Cmin value above 3000 ng/mL and even more above 3500 ng/mL the risk of adverse events is outweighing the therapeutic benefit of high Imatinib blood levels.

Preferably, the Ph+ leukemia is Philadelphia chromosome Ph+ ALL or, preferably, CML.

In one embodiment of the present invention, the predetermined fixed amount referred to herein under step (a) represents a therapeutically effective amount.

Throughout the present invention, preferably the mono-mesylate salt of Imatinib is used in step (a), e.g. in an oral daily dose of between 200 and 800 mg, preferably in a daily dose of 400 mg.

The methods described herein are particularly beneficial for CML patients having an Intermediate Sokal score (ISS). Methods to determine the ISS are known to the person skilled in the art.

Imatinib is specifically disclosed in the patent applications U.S. Pat. No. 5,521,184, the subject-matter of which is hereby incorporated into the present application by reference. Imatinib can also be prepared in accordance with the processes disclosed in WO03/066613.

For the purpose of the present invention, Imatinib is preferably applied in the form of its mono-mesylate salt. Imatinib mono-mesylate can also be prepared in accordance with the processes disclosed in U.S. Pat. No. 6,894,051 the subject-matter of which is hereby incorporated into the present application by reference. Comprised are likewise the corresponding polymorphs, e.g. crystal modifications, which are disclosed therein.

In step (a) of the method described above, in particular a daily dose of between 200 and 800 mg, e.g. 400 mg, of the mono-mesylate salt of Imatinib is administered orally. Imatinib monomesylate can be administered in dosage forms as described in U.S. Pat. No. 5,521,184, U.S. Pat. No. 6,894,051, US 2005-0267125 or WO2006/121941.

The collection of a blood sample from CML patients required under step (b) of the methods described herein can be accomplished by standard procedures being state of the art. A suitable procedure for the determination of the plasma trough level Cmin of Imatinib and N-{5-[4-(piperazino-methyl)-benzoylamido]-2-methylphenyl}-4-(3-pyridyl)-2-pyrimidine-amine is described by R. Bakhtiar R et al. in J Chromatogr B Analyt Technol Biomed Life Sci. 2002 Mar. 5; 768(2):325-40.

What is claimed is:

1. A method of treating a Philadelphia chromosome positive (Ph+) leukemia in a human patient suffering from Ph+ leukemia comprising the steps of:
(a) administering a predetermined fixed amount of Imatinib mesylate of between 200 and 800 mg to the human patient,
(b) collecting at least one blood sample from the patient,
(c) determining the plasma trough level (Cmin) of Imatinib mesylate,
(d) determining octamer binding protein activity, (OCT-1 Activity) in the at least one blood sample, and
(e) adjusting the dose of Imatinib mesylate applied to the individual patient in a manner that an Imatinib mesylate Cmin value is achieved in the patient of between 1000 and 3000 ng/mL, if in step (c) an Imatinib mesylate Cmin value of less then 1000 ng/mL is found and in step (d) an OCT-1 Activity is found below 6.0 to 10.0 ng/200,000 cells.

2. The method according to claim 1 wherein in step (a) a daily dose of 400 mg of Imatinib mesylate is administered daily.

3. A method of treating chronic myeloid leukemia (CML) in a human patient suffering from CML comprising the steps of:
(a) administering a predetermined fixed amount of Imatinib mesylate of between 200 and 800 mg to the human patient,
(b) collecting at least one blood sample from the patient,
(c) determining the plasma trough level (Cmin) of Imatinib mesylate,
(d) determining octamer binding protein activity, (OCT-1 Activity) in the at least one blood sample, and
(e) adjusting the dose of Imatinib mesylate applied to the individual patient in a manner that an Imatinib mesylate Cmin value is achieved in the patient of between 1000 and 3000 ng/mL, if in step (c) an Imatinib mesylate Cmin value of less than 1000 ng/mL is found and in step (d) an OCT-1 Activity is found below 6.0 to 10.0 ng/200,000 cells.

4. The method according to claim 3 wherein in step (a) a daily dose of 400 mg of Imatinib mesylate is administered daily.

5. A method of treating Philadelphia chromosome positive acute lymphoblastic leukemia (Ph+ ALL) in a human patient suffering from Ph+ ALL comprising the steps of:
(a) administering a predetermined fixed amount of Imatinib mesylate of between 200 and 800 mg to the human patient,
(b) collecting at least one blood sample from the patient,
(c) determining the plasma trough level (Cmin) of Imatinib mesylate,
(d) determining octamer binding protein activity, (OCT-1 Activity) in the at least one blood sample, and
(e) adjusting the dose of Imatinib mesylate applied to the individual patient in a manner that an Imatinib mesylate Cmin value is achieved in the patient of between 1000 and 3000 ng/mL, if in step (c) an Imatinib mesylate Cmin value of less than 1000 ng/mL is found and in step (d) an OCT-1 Activity is found below 6.0 to 10.0 ng/200,000 cells.

6. The method according to claim 5 wherein in step (a) a daily dose of 400 mg of Imatinib mesylate is administered daily.

* * * * *